United States Patent
Erdmann et al.

(10) Patent No.: US 11,990,242 B2
(45) Date of Patent: May 21, 2024

(54) REDUCING THE RISK OF POTENTIALLY PREVENTABLE EVENTS

(71) Applicant: CERNER INNOVATION, INC., Kansas City, KS (US)

(72) Inventors: Cole A. Erdmann, Kansas City, MO (US); Timothy J. Arnold, Chicago, IL (US); Xinyong Tian, Wilmette, IL (US)

(73) Assignee: Cerner Innovation, Inc., Kansas City, MO (US)

( * ) Notice: Subject to any disclaimer, the term of this patent is extended or adjusted under 35 U.S.C. 154(b) by 1142 days.

(21) Appl. No.: 15/685,532

(22) Filed: Aug. 24, 2017

(65) Prior Publication Data

US 2019/0065691 A1   Feb. 28, 2019

(51) Int. Cl.
*G16H 50/30*   (2018.01)
*G16H 10/60*   (2018.01)
*G16H 40/20*   (2018.01)
*G16H 40/67*   (2018.01)

(52) U.S. Cl.
CPC ............. *G16H 50/30* (2018.01); *G16H 10/60* (2018.01); *G16H 40/20* (2018.01); *G16H 40/67* (2018.01)

(58) Field of Classification Search
CPC ........ G16H 50/30; G16H 40/67; G16H 40/20; G16H 10/60
See application file for complete search history.

(56) References Cited

U.S. PATENT DOCUMENTS

| | | | |
|---|---|---|---|
| 9,336,482 B1* | 5/2016 | Corrado | G06N 3/0427 |
| 10,402,721 B2* | 9/2019 | Corrado | G16H 50/30 |
| 2001/0020229 A1* | 9/2001 | Lash | G16H 50/70 705/3 |
| 2004/0249669 A1* | 12/2004 | Pollack | G16H 20/10 705/2 |
| 2014/0303988 A1* | 10/2014 | Maneri | G16H 15/00 705/2 |
| 2015/0095046 A1* | 4/2015 | Pironti | G16H 50/30 705/2 |
| 2016/0117466 A1* | 4/2016 | Singh | G06Q 50/265 702/19 |
| 2017/0337345 A1* | 11/2017 | Pauws | G16H 50/20 |
| 2018/0277246 A1* | 9/2018 | Zhong | G16H 50/50 |

* cited by examiner

*Primary Examiner* — Rajesh Khattar
*Assistant Examiner* — Steven G. S. Sanghera
(74) *Attorney, Agent, or Firm* — Invoke (57) ABSTRACT

Methods, systems, and computer-storage media are provided for determining an individual's second event risk score where the second event risk score represents a likelihood that the individual will experience the second event within a predetermined time period after the occurrence of a first event. Upon occurrence of the first event, a sampling protocol is initiated where an electronic medical record store is accessed on a predetermined schedule to sample a pre-selected set of medical data elements for the individual. Logistic regression analysis is executed on the pre-selected set of medical data elements to generate a second event risk score for the individual. The second event risk score is communicated to a medical professional managing the medical care of the individual, and the individual's electronic medical record is modified to reflect the second event risk score.

17 Claims, 3 Drawing Sheets

REDUCING THE RISK OF POTENTIALLY PREVENTABLE EVENTS

BACKGROUND

Reducing the risk of multiple medical events occurring for an individual is a priority for those involved in the individual's medical care including the individual themselves, medical professionals, locations of treatment (hospitals, acute care facilities, etc.), and insurance companies. Evidence indicates an increasing demand for medical management of preventable events to reduce medical care costs and improve the medical status of individuals at risk. As such, identification of potentially preventable events through risk analysis is critical for more efficient and valuable management of medical care. Events that may be preventable through effective medical management may include hospitalizations, emergency department visits, admission to an acute care facility, admission to an inpatient rehabilitation facility, and repeat or emergency visits to medical professional practices.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Potentially preventable events may be prevented for individuals for a variety of medical conditions subsequent to a first event occurring. Some medical conditions that may be managed through medical management plans and result in effective prevention of multiple events following a first event may include asthma, diabetes, hypertension, myocardial infarctions, dehydration, pneumonia, and urinary tract infection. Additionally, early intervention for such conditions can prevent complications or the development of more severe medical diseases. As used herein, the term potentially preventable events may be defined as medical events that may be prevented (or their risk of recurrence reduced) with proper medical management after the occurrence of a first event.

Effective outpatient medical care management may result in preventing potential events from taking place. This may be accomplished by determining the risk of a certain medical event occurring based on the occurrence of a first event. For example, an analysis may be conducted on preselected medical data elements of an individual who experiences a first event, such as a hospital admission for congestive heart failure. The analysis of the preselected medical data elements generates a second event risk score indicating the likelihood of whether the individual may have a second event occur within a set time period.

At a high level, the present invention identifies a risk of a potentially preventable second event subsequent to the occurrence of a first event. By identifying the risk of a potentially preventable second event, outpatient care management can be utilized to reduce the occurrence of the second event as well as future events that may result in repeated hospitalization, emergency department visits, emergency visits to medical professional practices, or admission to acute care facilities/inpatient rehabilitation facilities. The process occurs by identifying that a first event has taken place and then determining the likelihood that a second event will occur within a predetermined timeframe. The result of identifying potentially preventable events is an overall decrease in spending on the medical care of an individual as well as an improved care experience for the individual.

The present invention targets a preselected population, which may be identified by a computer system or by medical professionals, and determines a second event risk score based on the occurrence of the first event in order to potentially prevent the second event from occurring within a predetermined timeframe (e.g. within 90 days after the first event occurring). Target populations may include individuals who are hospitalized, are at risk for acute hospitalization, suffer from chronic diseases which require on-going management (e.g. diabetes, heart failure), and multi-disease, multi-complication individuals (e.g. renal failure, individuals who have received transplants, cancer patients). Other examples of target populations include those individuals that have experienced one or more of the following conditions: pneumonia, congestive heart failure, urinary tract infections, chronic obstructive pulmonary disease (COPD), myocardial infarctions (heart attacks), dementia and Parkinson's disease.

Barriers encountered by medical professionals while managing the medical care of such populations include behavioral, social, adherence, and educational barriers. However, proper intervention and medical management after a first event based on a second event risk score determination may be able to overcome these barriers and prevent the second event from occurring.

Aspects herein describe computer-storage media, computerized methods, and computing systems that determine a second event risk score for an individual after the occurrence of a first event by using a pre-selected set of medical data elements stored in an electronic medical store. A computer system contains medical data elements for a pre-selected population that are stored in an electronic medical record store. A computer server is programmed to automatically access the electronic medical record store on a predetermined schedule to sample a pre-selected set of medical data elements for the pre-selected population after the occurrence of the first event. The computer server then automatically executes an analysis on the preselected set of medical data elements to generate a second event risk score for the individual following the occurrence of the first event. Then, in certain embodiments, the system may determine whether the second event risk score is greater than a predetermined risk score. A visually perceptible element representing the second event risk score is generated, and the second event risk score with the visually perceptible element is delivered to a browser window that displays the visually perceptible element. Finally, a notification is generated and communicated to a medical professional comprising the second event risk score. In some aspects, a notification is only generated for the medical professional when the second risk score is greater than the predetermined risk score.

As well, aspects herein are directed to using the second event risk score to automatically assign the individual to one of a high probability category, a moderate probability category, or a low probability category. In an additional aspect, the computer server may automatically generate one or more recommended medical interventions for the individual based on the individual's second event risk score and/or risk stratification. In yet additional aspects, the medical professional may be automatically prompted to create a customized medical management plan in response to the second event risk score and risk category assigned. Additionally, in other aspects, a notification regarding the second event risk score may be automatically communicated to the individual. As well, an appointment with the medical professional for follow up medical care may be automatically generated and communicated to the patient and/or the medical professional.

The server, as described herein, is further configured to access an electronic medical record (EMR) of the individual and modify the EMR to reflect the second event risk score, the risk category to which the individual is assigned, and/or any recommended clinical interventions. Subsequent computer users accessing the individual's EMR can quickly retrieve this information and use the information to guide individual medical care decisions such that the risk of the second event occurring for the individual is reduced. Moreover, by modifying the individual's EMR to reflect the second event risk score, the assigned risk category, and/or recommended medical interventions, improved computing system efficiencies are realized. For example, less computer "clicks" or entries to the EMR are needed by the computer user to review individual information in order to make a manual determination of whether the individual may be at risk for a second event, and/or to make manual determinations of appropriate medical interventions. Fewer "clicks" or entries reduce memory utilization, CPU cycles, number of operations that need to be performed by the computer, and power consumption by the computer.

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for computer-based medical information users to monitor an individual's risk for a second event to occur subsequent to a first event based on an analysis of pre-selected medical data elements. Following a first event, a server automatically accesses an electronic medical record store on a predetermined schedule to sample a pre-selected set of medical data elements. A logistic regression analysis is completed on the preselected set of medical data elements to generate a second risk score indicating the degree of risk that the second event will occur.

Figure 1:
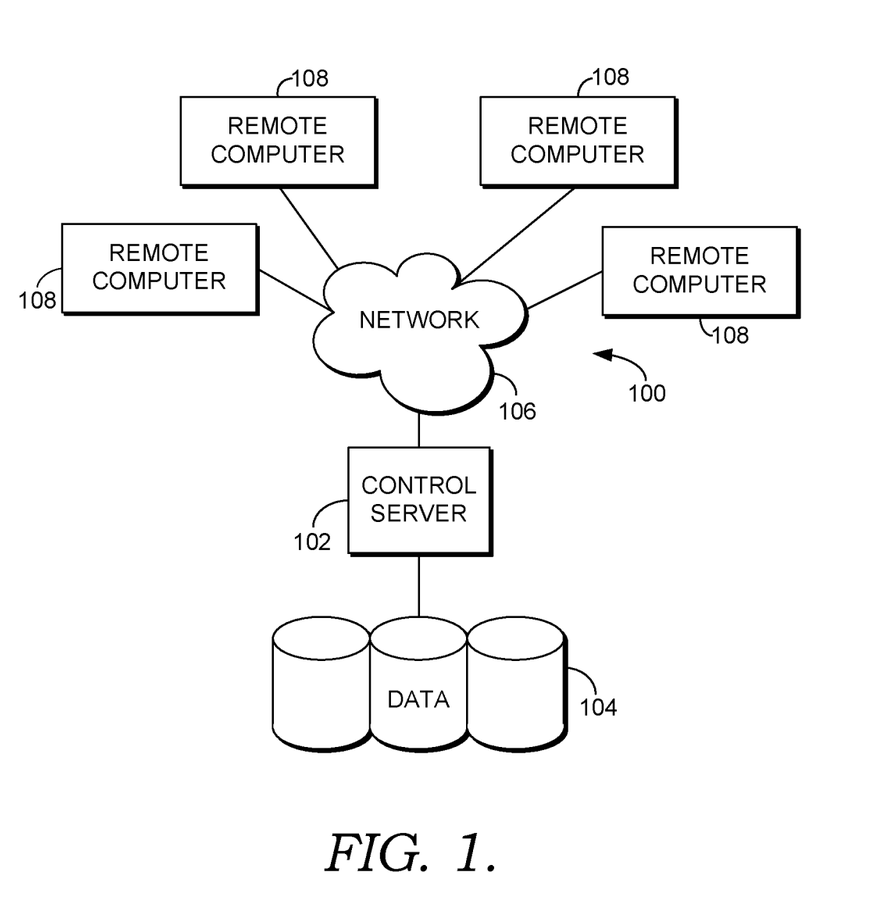
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present invention. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present invention to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and medical information workflows. The remote computers might also be physically located in traditional and nontraditional medical care environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Medical professionals may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
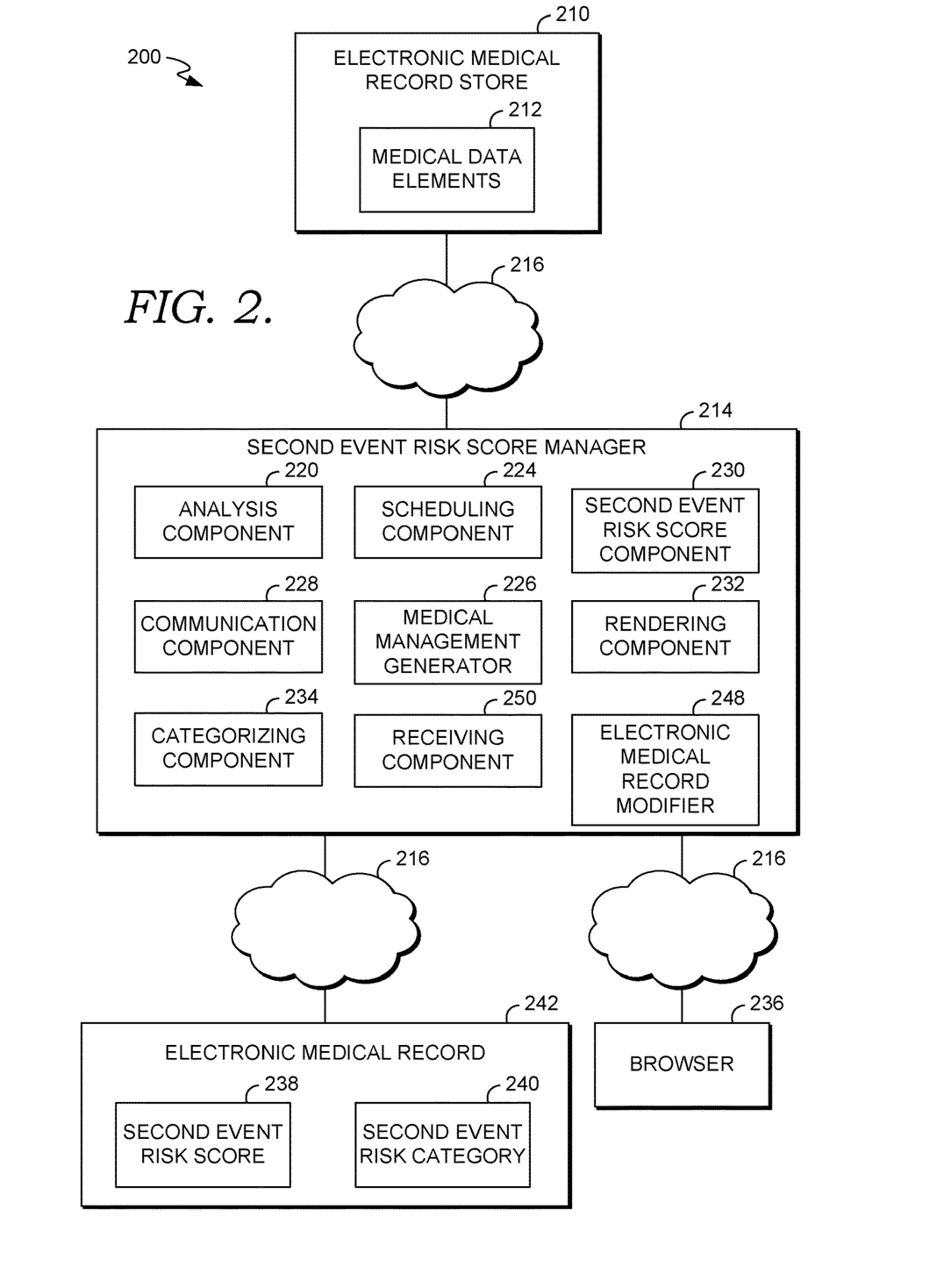
FIG. 2 is an exemplary system architecture suitable to implement embodiments of the present invention.

Turning now to FIG. 2, an exemplary computing system 200 is depicted. The computing system 200 is merely an example of one suitable computing system and is not intended to suggest any limitation as to the scope of use or functionality of embodiments of the present invention. Neither should the computing system 200 be interpreted as having any dependency or requirement related to any single component or combination of components illustrated herein.

The computing system 200 includes an electronic medical record store 210, a second event risk manager 214, and an electronic medical record 242. The electronic medical record store 210 is comprised of medical data elements 212. In this embodiment, the second event risk manager 214 is comprised of an analysis component 220, a scheduling component 224, a second event risk score component 230, a communication component 228, a medical management generator 226, a rendering component 232, a categorizing component 234, a receiving component 250, and an electronic medical record modifier 248. In other embodiments, the second event risk manager 214 may include any number of components necessary for the analysis and determination of a second event risk score. In this exemplary aspect, the electronic medical record 242 includes at least a second event risk score 238 data element and a second event risk category 240 data element. Finally, the computer system 200 may further include one or more browser windows 236 configured to display at least one visual perceptible element.

In some embodiments, one or more of the illustrated components may be implemented as a stand-alone application. The components described are exemplary in nature and in number and should not be construed as limiting. Any number of components may be employed to achieve the desired functionality within the scope of the embodiments hereof. Further, components may be located on any number of servers.

In aspects, the electronic medical record store 210 stores medical data elements 212 for individuals that have had a first event take place. First events include, but are not limited to, hospitalization, emergency department visits, admission to inpatient care facilities or rehabilitation facilities, and emergency visits at medical professional practices. First events may also include the occurrence of a predetermined list of medical conditions such as pneumonia, congestive heart failure, urinary tract infections, chronic obstructive pulmonary disease (COPD), myocardial infarctions (heart attacks), dementia and Parkinson's disease. The medical data elements 212 may be supplied by the electronic medical record (EMR) 242 of the individual. The EMR 242 of an individual may comprise, for instance, medical records from the medical professionals managing the individual's medical care (e.g. primary care, specialists, etc.), pharmacy records, hospital admission records, and the like. When a designated first event takes place for the individual, medical records stored in the individual's EMR 242 may be communicated to the electronic medical record store 210 and/or the second event risk score manager 214.

The medical data elements 212 stored in the electronic medical record store 210 may comprise, in exemplary aspects, medication information, vital sign information, demographic information, laboratory and/or procedure values and results, medical history (symptoms, diagnoses, and the like), vital signs, medication history, medical procedure history, social determinants (health literacy, behavioral factors, support network, and the like) and assessment information for the individual. More detail regarding the medical data elements 212 will be provided below.

In this aspect, the second event risk score manager 214 is comprised of nine subcomponents (listed above). However, in other aspects, the second event risk score manager 214 may be comprised of more or less components and any and all variations are contemplated herein. It will be appreciated that some or all of the subcomponents of the second event risk score manager 214 may be accessed via the network 216 and may reside on one or more devices. The second event risk score manager 214 can perform risk surveillance on some or all of the individuals in a pre-selected population and is in communication with the electronic medical record store 210, the browser 236, and the electronic medical record 242 via the network 216.

When the individual has a designated first event occur, the electronic medical record store 210 is configured to communicate a signal to the receiving component 250 where the signal comprises an indication that the individual has had a first event occur. This communication may occur simultaneously with or after the occurrence of the first event. Additionally, the signal may be communicated to the receiving component 250 in a variety of ways. Some examples include, but are not limited to: a medical professional documenting that the first event has occurred in the electronic medical record 242, a recording from a medical device such as an echocardiogram machine indicating that a patient may be having a first event (e.g. heart attack), the recording of lab values after testing, and the like.

The receiving component 250 is further configured to receive and/or access medical data elements 212 regarding the individual during and after the occurrence of the first event. For instance, the receiving component 250 is configured to receive medical data elements 212 from the electronic medical record store 210 where the medical data elements 212 comprise at least demographic information, lab results, medical history, vital signs, medications, social determinants, and procedures.

After the receiving component 250 receives medical data elements 212 regarding the individual's first event, the scheduling component 224 is configured to access the electronic medical record store 210 on a predetermined schedule to sample a pre-selected set of medical data elements 212 for the individual. In exemplary aspects, the scheduling component 224 begins sampling on the predetermined schedule subsequent to the receiving component 250 receiving a signal from the electronic medical record store 210 or the electronic medical record 242 indicating that the first event has taken place. For instance, the scheduling component 224 may begin accessing the electronic medical record store 210 within at least 24 hours of the occurrence of the first event. Sampling schedules may vary but, in exemplary aspects, may comprise continuously, every 10 minutes, every 30 minutes, every hour, every couple of hours, once daily, and the like, although sampling schedules outside these values or between these values are contemplated herein.

The pre-selected set of medical data elements 212 may comprise medication data elements, laboratory data elements, demographic data elements, assessment data elements, vital sign data elements, medical history data elements, social determinant data elements, procedure data elements, and the like. Data elements are included within the pre-selected set if they are found to have statistical significance ($P<0.05$) in predicting the probability of the occurrence of a second event related to the first event. Medication data elements may comprise medications that the individual is taking while at the time of the first event, and may include oral medications as well as intra-venous (IV) medications. The laboratory data elements may comprise lab values obtained for the individual at the time of the first event or shortly after. In exemplary aspects, the laboratory data elements in the pre-selected set may comprise chloride levels, creatinine levels, white blood cell counts, neutrophil counts, glucose values, troponin values, and prothrombin times.

The demographic data elements in the pre-selected set may comprise gender information, whether the individual is black, Hispanic, or other race and whether the gender's demographic data has any medical implications. Vital sign data elements in the pre-selected set comprise the most recent temperature reading, blood pressure reading, pulse reading, oxygen level ($pO_2$), respiratory rate, symptoms leading up to the first event, current symptoms, and medical treatment plan responding to the first event.

Medical history data elements in the pre-selected set may comprise whether medication reconciliation was performed upon the occurrence of the first event. The medical history data elements may further include family history, symptoms prior to the first event, medication history, diagnoses, previous medical treatment plans, and any other pertinent information. Additionally, procedure data elements include past medical procedures that the individual has undergone, including surgeries and non-invasive procedures.

Social determinant data elements in the pre-selected set may comprise health literacy, behavioral factors, support network, and any other component which may play a role in the individual's current condition, in the occurrence of the first event itself, in the recovery time period subsequent to the first event, and in the future regarding general medical management for the individual. These elements may play a role in the risk of a second event happening.

The number of medical data elements 212 included in the pre-selected set may be variable. For instance, the pre-selected set described above comprises approximately six medical data elements groupings with any number of discrete data elements within each grouping. However, the pre-selected set may comprise any number of medical data elements, where each data element has been shown to have statistical significance in predicting the individual's second event risk. Additionally, the medical data element groupings may be customized and vary based on the particular first event that has occurred. By way of illustrative example and not by limitation, the medical data elements groupings for an individual where the first event is diabetic shock may include health literacy within the medical data elements 212. In this situation, health literacy may be a more important factor than it would be in other situations such as, for instance, a urinary tract infection, and may have a greater significance in determining the second event risk score. Any and all aspects, and any variation thereof, are contemplated as being within the scope herein.

Once the electronic medical record store 210 has been accessed via the scheduling component 224 and the pre-selected set of medical data elements 212 has been sampled, the analysis component 220 executes a logistic regression algorithm on the pre-selected set of medical data elements 212 to generate a second event risk score for the individual. The analysis component 220 may be configured to execute the logistic regression algorithm at the time the pre-selected set of medical data elements are sampled by the scheduling component 224. Alternatively, the logistic regression analysis by the analysis component 220 may be configured to occur on a predetermined schedule. Further, such analysis may be repeated based upon updates to the medical data elements 212. Any and all aspects, and any variation thereof, are contemplated as being within the scope herein.

In exemplary aspects, prior to executing the logistic regression algorithm, the analysis component 220 is configured to assign a weight to one or more of the medical data element within the pre-selected set that reflects its importance to the risk of the second event occurring. For example, an abnormal respiratory rate may be weighted more heavily than the individual's gender. The second event risk score comprises a number between 0 and 1 and indicates the probability of the second event occurring. Accordingly, a second event risk score of 0.1 indicates a low probability of having the event occur, while a second event risk score of 0.8 indicates a high probability that the second event will occur.

In certain aspects, once the second event risk score is generated by the analysis component 220, the second event risk score component 230 automatically calculates whether the second event risk score generated is greater than a predetermined risk score. The predetermined risk score may represent a certain threshold risk score above which the individual is more likely to have the second event occur after the first event based on their medical condition or nature of the first event. If the calculated second event risk score is above the predetermined risk score, then a notification may be generated and communicated to a medical professional. In exemplary aspects, the value of the second event risk score may be directly correlated with the probability that the second event for occur. For example, if the second event risk score is 0.8, then the probability of the second even occurring may be, for example, 80%.

Depending on the nature of the first event, a threshold predetermined risk score may vary. For instance, an individual experiencing a severe asthma attack which requires hospitalization may have a higher predetermined risk score (e.g. 0.7) threshold than an individual who has recently had a heart attack (e.g. 0.3). In this example, if the first event was a heart attack and the analysis component 220 generated a second event risk score of 0.6, the communication component 228 would generate and communicate a notification to a medical professional that the individual has a calculated second event risk score of 0.6, which exceeded the 0.3 preselected threshold risk score, indicating that the individual was at a more significant risk for a second heart attack event occurring.

Further, as discussed below, the notification may further comprise a risk category, determined by the categorizing component 234. The categorizing component 234 is configured to utilize the second event risk score 238 and/or the nature of the event to determine a risk probability category and assign the individual to a specific category of low probability, moderate probability, or high probability. Generally, an individual having a second event risk score between 0 and 0.3 may be categorized in the low probability risk category, an individual having second event risk score between 0.3 and 0.6 may be categorized in the moderate probability risk category, and an individual with a s second event risk score between 0.6 and 1.0 may be categorized in the high probability risk category. However, the category assigned by the categorizing component 234 may vary based on the nature of the first event, the second event risk score 238, and the predetermined risk score threshold. For example, a second event risk score 238 of a 0.5 may fall within the high risk category for an individual whose first event was a heart attack. By contrast, a second event risk score 238 of 0.5 may fall within the moderate risk category for another individual whose first event was an asthma attack. These ranges are exemplary only and it is contemplated that the stratification scheme may be based on other ranges.

In an additional exemplary aspect, the categorizing component 234 is further configured to modify the assigned risk category based on, for example, the individual's first event diagnosis as indicated by, for example, an ICD9 code, and/or the individual's co-morbidity information received by the receiving component 250. This information may not be received by the receiving component 250 until several days after the first event occurs and/or until after an initial second event risk score has been generated for the individual.

In an exemplary aspect, ICD9 codes may be limited to codes that have been found to be statistically significant (P<0.05) in predicting the probability of a second event occurring. In exemplary aspects, the ICD9 codes may be limited to codes indicating nervous disorders, cerebrovascular disease, heart disease, liver disease, cancer, arthritis, and gastrointestinal disorders. This is an exemplary list only, and it is contemplated herein that other ICD9 codes may be included in the pre-selected set.

Upon receiving the notification from the communication component 228, the medical professional may customize a medical management plan for the individual based on the second event risk score 238. Alternatively, a medical management plan generator 226 may generate an automated medical management plan for the individual based on the second event risk score 238. Finally, in some aspects, the communication component 228 may generate and communicate a notification to the individual comprising the second event risk score. Such communication may additionally comprise the automated or customized medical management plan approved by the medical professional and/or the option to follow up with the medical professional regarding management of their medical care in order to try to prevent the second event from occurring.

Although not shown, it is contemplated herein that the medical management generator 226 is further configured to use the individual's second event risk score and/or risk stratification to automatically and without human intervention generate one or more medical recommendations to reduce the individual's risk for the second event. These medical recommendations may be communicated to the medical professional, individual or both.

The rendering component 232 is configured to represent the outputs of at least the second event risk score component 230, the categorizing component 234, and the medical management generator 226 with visually perceptible elements and to communicate the visually perceptible elements to the browser 236 such that the visually perceptible elements are displayed to an end user such as a medical professional caring for the individual. More particularly, the individual's second event risk score may be represented by a first visually perceptible element, the individual's risk stratification may be represented by a second visually perceptible element, and any medical recommendations may be represented by a third visually perceptible element.

The EMR modifier component 248 is configured to access the individual's electronic medical record 242 and electronically modify the individual's EMR to reflect, for example, the individual's second event risk score 238, the individual's second event risk category 240, and/or any medical recommendations generated for the individual based on the second event risk score 238 and/or the second event risk category 240. Modifying the individual's EMR 242 may comprise, for instance, modifying an existing data element within the EMR 242, adding a new data element to the EMR 242, and/or overwriting an existing data element with a new data element. Any and all aspects, and any variation thereof, are contemplated as being within the scope herein. By modifying the individual's EMR 242 to reflect at least the second event risk score 238 and/or the individual's second event risk category 240, subsequent computer users accessing the individual's EMR 242 can quickly retrieve these data elements. This, in turn, reduces the users' navigational burdens associated with accessing and compiling information in an attempt to determine whether the individual is at risk for a second event during the predetermined timeframe (e.g. 90 days after the first event). By reducing navigation burdens (e.g. user clicks or entries), computer processing speeds are improved, power consumption is decreased, and memory usage is decreased.

Figure 3:
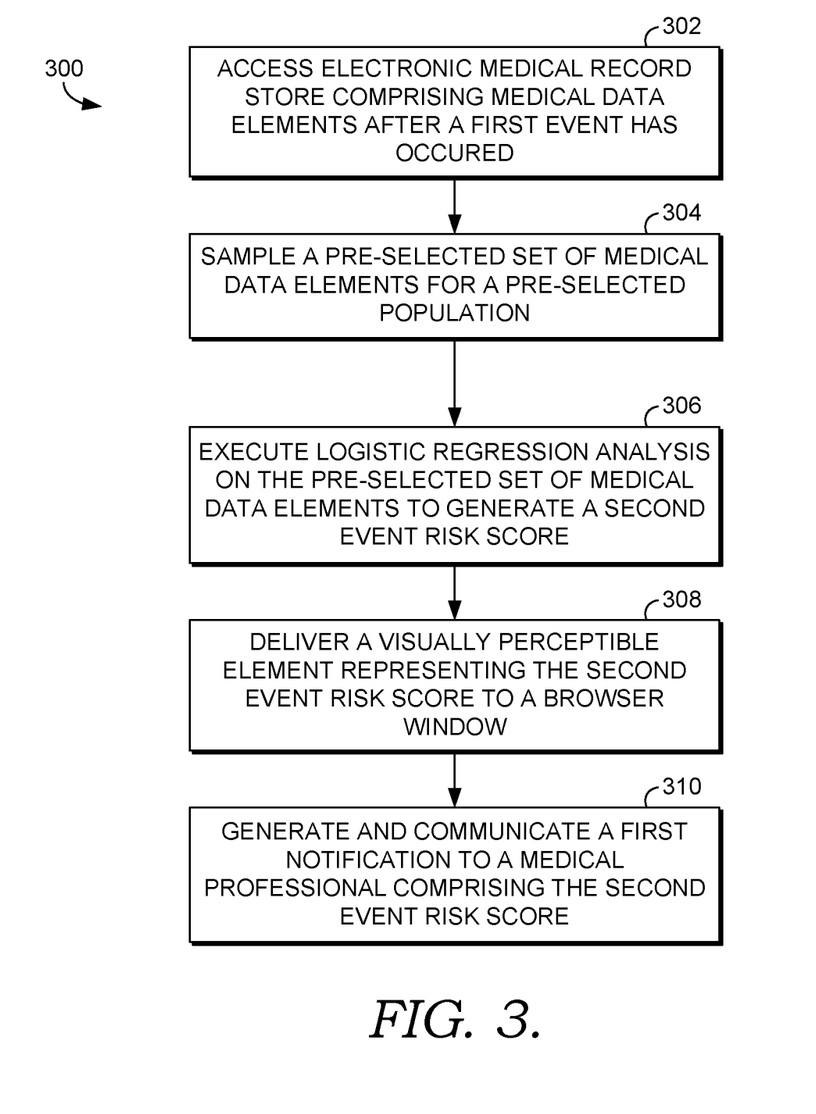
FIG. 3 is a flow diagram depicting an exemplary method of executing embodiments of the present invention.

Turning now to FIG. 3, a flow diagram is depicted of an exemplary method 300 of generating and serving a second event risk score to, for instance, a medical professional managing the medical care of an individual who has experienced a first event. The method 300 may be implemented by the computing system architecture 200 described with respect to FIG. 2.

At a step 302, upon the occurrence of a first event, an electronic medical record store, such as the electronic medical record store 210 in FIG. 2, containing medical data elements is accessed by a component, such as the receiving component 250 in FIG. 2. The electronic medical record store comprises medical data elements for the individuals being cared for. After this, at a step 304, a component, such as the scheduling component 224 in FIG. 2, samples a pre-selected set of medical data elements for a pre-selected population.

At a step 306, a component, such as the analyzing component 220 in FIG. 2, executes a logistic regression analysis on the pre-selected set of medical data elements to generate a second event risk score for the individual, where the second event risk score represents a probability of the individual having a second event occurring within a predetermined timeframe. In exemplary aspects, the logistic regression analysis may be executed after weights have been assigned to the medical data elements within the pre-selected set. At step 308, a visually perceptible element representing the second event risk score is delivered to a browser window. The visually perceptible element may be generated by a rendering component such as the rendering component 232 of FIG. 2. Finally, at step 310, a first notification comprising the second event risk score is generated and communicated by, for example, a communication component such as the communication component 228, to the medical professional.

Notifications may be generated for medical professionals comprising the second event risk score for a variety of first events. Ideally, the notification to a medical professional of the second event risk score indicating that the individual is at risk for a second event occurring within the predicted timeframe after the first event will trigger outpatient care management plans that will prevent or reduce the chances of the potentially preventable second event from occurring. For example, the system may generate a high risk second event risk score for an individual who experiences an acute asthma attack that results in hospitalization. This high risk second event risk score will indicate to the medical professional that based on the individual's current medical state, there is a high probability that a second event will occur. This second event may include the reoccurrence of a severe asthma attack resulting in hospital admission or other potentially preventable events that are related to the first asthma attack event such as exacerbations, worsening of symptoms, or emergency department visits. Intervention by the medical professional to manage the medical care of the individual after the first event may result in the prevention of the potentially preventable event within the predetermined time frame of 90 days. While the predetermined timeframe discussed herein is 90 days, it is contemplated that the timeframe post-first event to analyze for the determination of the risk score of a second event may comprise any variety of time periods, including shorter and longer timeframes.

The method 300 may further include (not shown), the additional steps of accessing the individual's EMR, and modifying the EMR to reflect the second event risk score. The EMR may be accessed, for example by, for instance, the electronic medical record modifier 248 in FIG. 2, which may input the second event risk score and second event risk category generated, making the information available for anyone with access to the electronic medical record. Updating the individual's EMR with such information is particularly important when the individual presents with a complicated medical history or is being managed by multiple medical professionals. Recording this information efficiently and effectively into the EMR communicates relevant information to medical professionals so that considerations may be made in the medical management of the individual and to prevent future events from occurring.

The method 300 may further comprise, a component such as the categorizing component in 234 in FIG. 2, that utilizes the second event risk score to assign the individual to one of a high risk category, a moderate risk category, and a low risk category. The individual's EMR may be further modified to reflect the individual's risk category assignment. Additionally, the individual's risk category assignment may be represented by a second visually perceptible element which is served to the browser window such that it can be displayed.

In aspects where the system sends a notification to the individual comprising the second event risk score and/or the risk score category, the individual may have the option of scheduling a follow up appointment with the medical professional managing their medical care or the system may automatically create an appointment for the individual. By initiating a follow up appointment with the medical professional, the system ensures that the individual is promptly seen so that outpatient care management can continue or begin in an effective manner to decrease the chances of the second event occurring within the predetermined timeframe. The second event may also be preventable through measures such as cessation of risk increasing activity (e.g. smoking for an individual who suffers from COPD), adherence and/or access to medication, education regarding the individual's medical condition, and symptom management. This not only improves the medical care of the individual, but will also result in decreased medical care costs and more efficient medical management as active outpatient care will lead to a decrease in the occurrence of potentially preventable events. Additionally, evidence suggests that in-person contact between the individual and medical professional is more effective than telephonic contact and decreases the risk of future events and medical care costs.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system for generating a second event risk score for an individual, the system comprising:
   an electronic medical record store comprising a plurality of medical data elements for the individual, the plurality of medical data elements comprising demographic data, medication data, laboratory data, medical history data, and social determinant data,
      wherein the electronic medical record store determines that the individual is currently experiencing an occurrence of a designated first medical event based on information provided to the electronic medical record store, the information being provided by a medical device, the information being collected from the individual by the medical device while being connected to the individual, the designated first medical event being a medical emergency;
      wherein in response to determining the occurrence of the designated first medical event for the individual and during the occurrence of the designated first medical event, the electronic medical record store generates and communicates a signal comprising an indication of the occurrence of the designated first medical event; and
   a computer server coupled to the electronic medical record store and programmed to, via one or more processors of the computer server:
      receive the signal from the electronic medical record store comprising the indication of the occurrence of the designated first medical event for the individual during the occurrence of the designated first medical event;
      in response to receiving the signal from the electronic medical record store of the occurrence of the designated first medical event and during the occurrence of the designated first medical event, automatically access the electronic medical record store;
      sample, from the plurality of medical data elements in the electronic medical record store, a pre-selected set of medical data elements having a statistical significance of at least $P<0.05$ for predicting a probability of occurrence of a second event based on the occurrence of the designated first medical event;
      generate a second event risk score for the individual by performing a logistical regression analysis of the pre-selected set of medical elements that are sampled from the electronic medical record store, wherein the second event risk score indicates the probability of occurrence of the second event for the individual;
      assign the second event risk score to one of a low probability risk category, a moderate probability risk category, or a high probability risk category, wherein the low probability risk category corresponds to the second event risk score in a first range, the moderate probability risk category corresponds to the second event risk score in a second range, and the high probability risk category corresponds to the second event risk score in a third range, wherein a value of the second event risk score in the third range is greater than a value of the second event risk score in the second range, and a value of the second event risk score in the second range is greater than a value of the second event risk score in the first range;
      access an electronic medical record (EMR) for the individual;
      modify the EMR to include the second event risk score and the one of the low probability risk category, the moderate probability risk category, or the high probability risk category that is assigned, wherein modification of the EMR for the individual includes one or more of modifying an existing data element, adding a new data element, or overriding an existing data element with a new data element within the EMR;
      generate a first visually perceptible element that represents the second event risk score and a second visually perceptible element that represents whether the second event risk score is assigned to the low probability category, the moderate probability category, or the high probability category;

deliver the first visually perceptible element and the second visually perceptible element to a browser window to cause display to a user of the first visually perceptible element and the second visually perceptible element for the individual;

generate and communicate a first notification to a medical professional when the second event risk score meets or exceeds a predetermined threshold; and generate an automated medical management plan for the individual based on the second event risk score, wherein the individual is treated in accordance with the automated medical management plan.

2. The system of claim 1, wherein the electronic medical record store is associated with at least one selected from: a hospital, an inpatient rehabilitation facility, an acute care facility, a pharmacy, and a medical professional practice.

3. The system of claim 1, wherein the second event risk score comprises a probability that the individual will have a second event occur within 90 days after the designated first medical event.

4. The system of claim 1, further wherein a notification comprising the second event risk score is generated and communicated to the individual.

5. The system of claim 1, wherein the medical professional generates a customized medical management plan for the individual based on the second event risk score.

6. The system of claim 1, wherein one or more medical data elements within the pre-selected set of medical data elements is assigned a weight coefficient.

7. The system of claim 6, wherein a higher weight coefficient is associated with a medical data element that increases the risk of a second event more than a medical data element associated with a lower weight coefficient.

8. One or more non-transitory computer-storage media having computer-usable instructions that, when used by one or more computing devices, cause the one or more computing devices to perform a method for determining a second event risk score for an individual, the method comprising:

automatically accessing an electronic medical record store containing a plurality of medical data elements for the individual, the plurality of medical data elements comprising demographic data, medication data, laboratory data, medical history data, and social determinant data;

determining that the individual is currently experiencing an occurrence of a designated first medical event based on information provided to the electronic medical record store, the information being provided by a medical device, the information being collected from the individual by the medical device while being connected to the individual, wherein the designated first medical event is a medical emergency;

in response to determining the occurrence of the designated first medical event for the individual by the electronic medical record store and during the occurrence of the designated first medical event, generating and communicating a signal comprising an indication of the occurrence of the designated first medical event;

in response to receiving the indication of the occurrence of the designate first medical event for the individual and during the occurrence of the designated first medical event, automatically sampling, from the plurality of medical data elements in the electronic medical record store, a pre-selected set of medical data elements having a statistical significance of at least $P<0.05$ for predicting a probability of occurrence of a second medical event based on the occurrence of the designated first medical event;

generating a second event risk score for the individual by performing a logistical regression analysis of the pre-selected set of medical elements sampled from the electronic medical record store, wherein the second event risk score indicates the probability of occurrence of the second medical event for the individual;

assigning the second event risk score to one of a low probability risk category, a moderate probability risk category, or a high probability risk category, wherein the low probability risk category corresponds to the second event risk score in a first range, the moderate probability risk category corresponds to the second event risk score in a second range, and the high probability risk category corresponds to the second event risk score in a third range, wherein a value of the second event risk score in the third range is greater than a value of the second event risk score in the second range, and a value of the second event risk score in the second range is greater than a value of the second event risk score in the first range;

accessing an electronic medical record (EMR) for the individual;

modifying the EMR to include the second event risk score and the one of the low probability risk category, the moderate probability risk category, or the high probability risk category that is assigned, wherein modification of the EMR for the individual includes one or more of modifying an existing data element, adding a new data element, or overriding an existing data element with a new data element within the EMR;

generating a first visually perceptible element that represents the second event risk score and a second visually perceptible element that represents whether the second event risk score is assigned to the low probability risk category, the moderate probability risk category, or the high probability risk category;

delivering the first visually perceptible element and the second visually perceptible element to a browser window that displays the first and second visually perceptible elements;

generating and communicating at least a first alert comprising the second event risk score to a medical professional when the second event risk score meets or exceeds a predetermined threshold; and generating an automated medical management plan for the individual based on the second event risk score, wherein the individual is treated in accordance with the automated medical management plan.

9. A computerized method comprising:

determining that an individual is currently experiencing an occurrence of a designated first medical event based on information provided to an electronic medical record store, the information being provided by a medical device, the information being collected from the individual by the medical device while being connected to the individual, wherein the designated first medical event is a medical emergency;

in response to determining the occurrence of the designated first medical event for the individual by the electronic medical record store and during the occurrence of the designated first medical event, generating and communicating a signal comprising an indication of the occurrence of the designated first medical event;

receiving from the electronic medical record store the indication of the occurrence of the designated first medical event and during the occurrence of the designated first medical event;

incident to receiving the indication and within a predetermined period of time of receiving the indication, automatically initiating a computerized sampling protocol that samples a pre-selected set of medical data elements from a plurality of medical data elements associated with the individual and stored in an electronic medical record store, wherein the pre-selected set of medical data elements have a statistical significance of at least $P<0.05$ for predicting a probability of occurrence of a second event based on the occurrence of the designated first medical event, and wherein the plurality of medical data elements comprise demographic data, medication data, laboratory data, medical history data, and social determinant data;

generating a second event risk score for the individual by performing a logistical regression analysis of the pre-selected set of medical elements that are sampled from the electronic medical record store, wherein the second event risk score indicates the probability of occurrence of the second event for the individual;

assigning the second event risk score to one of a low probability risk category, a moderate probability risk category, or a high probability risk category, wherein the low probability risk category corresponds to the second event risk score in a first range, the moderate probability risk category corresponds to the second event risk score in a second range, and the high probability risk category corresponds to the second event risk score in a third range, wherein a value of the second event risk score in the third range is greater than a value of the second event risk score in the second range, and a value of the second event risk score in the second range is greater than a value of the second event risk score in the first range;

accessing an electronic medical record (EMR) for the individual;

modifying the EMR to include the second event risk score and the one of the low probability risk category, the moderate probability risk category, or the high probability risk category that is assigned, wherein modification of the EMR for the individual includes one or more of modifying an existing data element, adding a new data element, or overriding an existing data element with a new data element within the EMR;

generating a first visually perceptible element that represents the second event risk score and a second visually perceptible element that represents whether the second event risk score is assigned to the low probability risk category, the moderate probability risk category, or the high probability risk category;

delivering the first and second visually perceptible elements to a browser window that displays the first and second visually perceptible elements;

generating and communicating a notification comprising the second event risk score associated with the individual to a medical professional when the second event risk score meets or exceeds a predefined threshold; and generating an automated medical management plan for the individual based on the second event risk score, wherein the individual is treated in accordance with the automated medical management plan.

10. The method of claim 9, wherein the notification to the medical professional further comprises one or more of an option to customize a medical management plan, and an option to communicate a message to the individual containing the second event risk score and a medical management plan.

11. The method of claim 9, further comprising automatically creating an appointment for the individual with the medical professional when the second event risk score is greater than a predetermined risk score.

12. The system of claim 1, wherein the medical device is an echocardiogram machine and the designated first medical event is a heart attack.

13. The system of claim 1, wherein the first notification is communicated to the medical professional during the occurrence of the designated first medical event.

14. One or more non-transitory computer-storage media of claim 8, wherein the medical device is an echocardiogram machine and the designated first medical event is a heart attack.

15. One or more non-transitory computer-storage media of claim 8, wherein the first alert is communicated to the medical professional during the occurrence of the designated first medical event.

16. The method of claim 9, wherein the medical device is an echocardiogram machine and the designated first medical event is a heart attack.

17. The method of claim 9, wherein the notification is communicated to the medical professional during the occurrence of the designated first medical event.

* * * * *